United States Patent [19]
Yoshimura et al.

[11] 3,962,333
[45] *June 8, 1976

[54] PROCESS FOR THE PRODUCTION OF ACRYLAMIDE AND METHACRYLAMIDE

[75] Inventors: Kiyotaka Yoshimura, Fujisawa; Shiro Asano, ; Tadatoshi Honda, both of Yokohama, all of Japan

[73] Assignee: Mitsui Toatsu Chemicals, Incorporated, Tokyo, Japan

[ * ] Notice: The portion of the term of this patent subsequent to Oct. 7, 1992, has been disclaimed.

[22] Filed: Sept. 25, 1975

[21] Appl. No.: 617,973

Related U.S. Application Data

[63] Continuation-in-part of Ser. No. 205,137, Dec. 6, 1971, Pat. No. 3,911,009.

[30] Foreign Application Priority Data
Dec. 14, 1970 Japan.............................. 45-110514

[52] U.S. Cl............................................. 260/561 N
[51] Int. Cl.² ................................. C07C 103/08
[58] Field of Search ............................... 260/561 N

[56] References Cited
UNITED STATES PATENTS

| | | | |
|---|---|---|---|
| 3,381,034 | 4/1968 | Greene et al. ................. | 264/561 N |
| 3,597,481 | 8/1971 | Tefertiller et al. ............. | 260/561 N |
| 3,631,104 | 12/1971 | Hebermann et al. ........... | 260/561 N |
| 3,642,894 | 2/1972 | Hebermann et al. ........... | 260/561 N |
| 3,758,578 | 9/1973 | Hebermann et al. ........... | 260/561 N |
| 3,766,088 | 10/1973 | Yoshimura et al. ............ | 260/561 N |

FOREIGN PATENTS OR APPLICATIONS

| | | | |
|---|---|---|---|
| 2,036,126 | 2/1971 | Germany ....................... | 260/561 N |
| 45-21295 | 7/1970 | Japan............................. | 260/561 N |

*Primary Examiner*—C. Davis
*Attorney, Agent, or Firm*—Fisher, Christen & Sabol

[57] ABSTRACT

An improved process for preparing acrylamide or methacrylamide which process comprises the step of reacting acrylonitrile or methacrylonitrile with water in the presence of a catalyst system consisting of a metallic copper containing catalyst and a copper salt promoter, said copper salt being copper sulfate, copper nitrate, copper halide, or a copper salt of a lower fatty acid.

5 Claims, 1 Drawing Figure

U.S. Patent  June 8, 1976  3,962,333
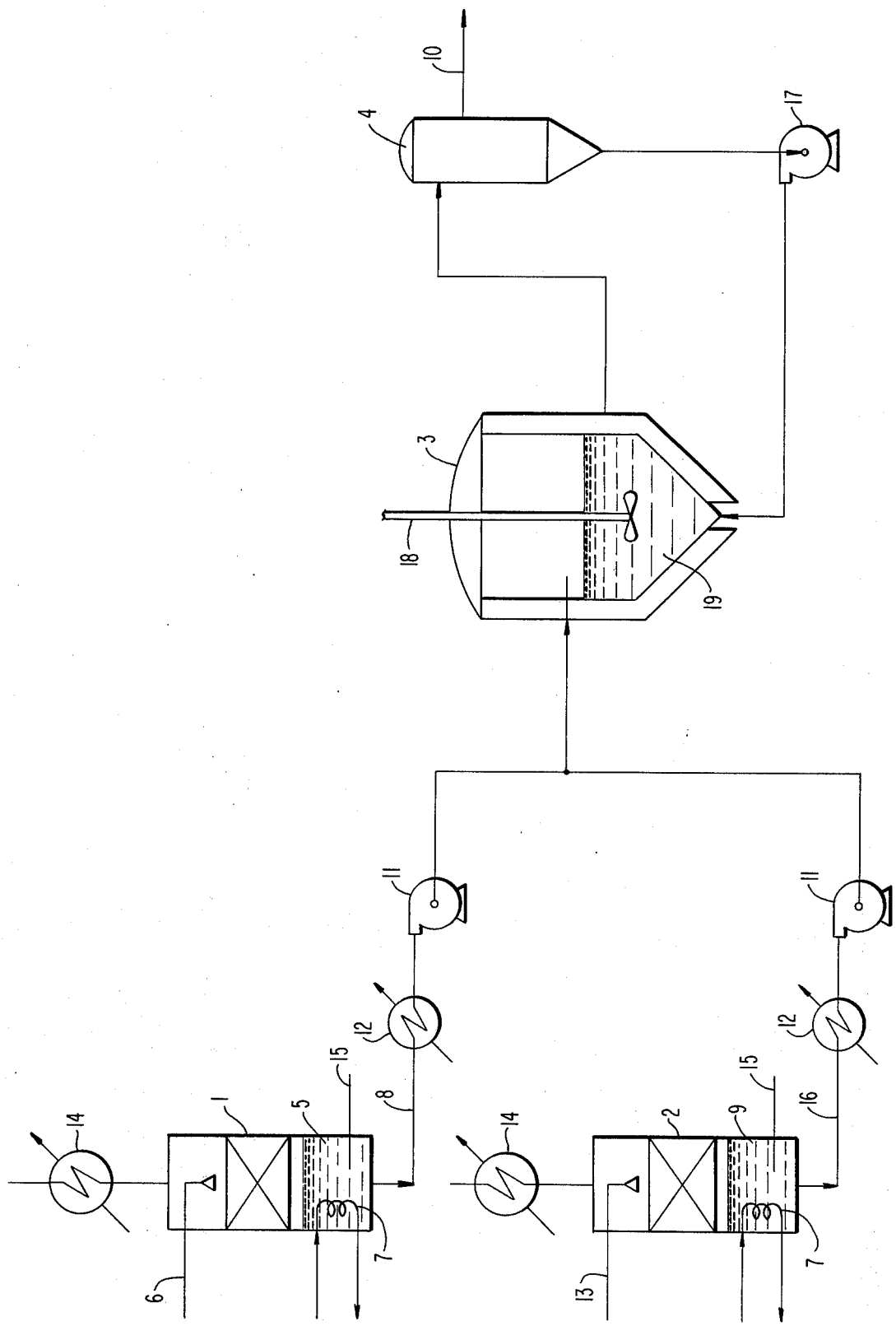

PROCESS FOR THE PRODUCTION OF ACRYLAMIDE AND METHACRYLAMIDE

CROSS REFERENCE TO RELATED APPLICATION

This application is a continuation-in-part of application Ser. No. 205,137 filed Dec. 6, 1971, now U.S. Pat. No. 3,911,009.

BACKGROUND OF THE INVENTION

1. Field of the Invention

The present invention relates to the preparation of acrylamide or methacrylamide by reacting acrylonitrile or methacrylonitrile with water in the presence of a metallic copper containing catalyst.

2. Description of the Prior Art

U.S. Pat. No. 3,381,034 teaches that cuprous ions catalyze the hydrolysis of nitriles and discloses that such ions may be provided by a cupric salt and copper metal. Metallic cooper alone was disclosed and exemplified to have no catalytic effect in the process, although the patentees could not explain tha advantages of the presence of copper metal when the cuprous ion was present. Reaction times on the order of 20 hours were usually necessary to obtain a conversion greater than 25 mol percent based on the nitrile.

It is known that acrylamide or methacrylamide may be prepared from acrylonitrile or methacrylonitrile in the presence of a copper metal catalyst. The copper catalysts suitable for the process include Raney copper, Ullmann copper, reduced copper, and copper catalysts containing metallic nickel, chromium, manganese, zinc, or molybdenum as well as oxides and sulfides of these metals or such catalysts supported on carriers (U.S. patent application Ser. No. 56,967, filed on July 21, 1970 owned by the assignee of the present application).

When acrylonitrile or methacrylonitrile is hydrated using one of the aforementioned catalysts, a reaction for producing acrylamide can be carried out in the presence of a very small amount of the copper catalyst, for example, about 0.01 g. of the copper catalyst based on 1 mol of acrylonitrile. However, a high conversion is not obtained, and in order to adopt this as an industrial process, a more effective catalyst system is desired.

SUMMARY OF THE INVENTION

An object of the present invention is to provide a novel catalyst system for preparing acrylamide or methacrylamide by reacting acrylonitrile or methacrylonitrile with water.

Another object of the present invention is to accelerate the reaction rate of the hydration of acrylonitrile or methacrylonitrile by improving the catalytic efficiency of copper catalysts, thereby advancing the economy of the process.

In the invention, acrylonitrile or methacrylonitrile is reacted with water in the presence of a catalyst system consisting of a copper containing catalyst of Raney copper, Ullmann copper, reduced copper, reduced copper oxide, copper containing (a) at least one metal selected from the group consisting of chromium and zinc or (b) a reduced oxide of said metal, and these catalysts supported on carriers and, as promoter, at least one copper salt selected from the group consisting of copper sulfate, copper nitrate, copper halide and a copper salt of a lower fatty acid. The amount of said copper salt should be below 400 ppm (parts per million) based upon the available water present and preferably less than 150 ppm to efficiently produce acrylamide or methacrylamide at a high yield. As little as 5 ppm significantly increases the rate of conversion and mol percent conversion. The term "copper" when used in reference to a copper ion, is intended to include both cuprous and cupric ions and mixtures thereof. When the amount of copper salt exceeds as little as about 500 ppm, tests have revealed that the promoter actually hinders the catalytic efficiency of copper catalysts.

BRIEF DESCRIPTION OF THE DRAWING

FIG. 1 is a flow sheet of one embodiment of the present invention.

DESCRIPTION OF THE PREFERRED EMBODIMENTS

Copper salts useful as promoters in the present invention include cuprous and/or cupric nitrate or sulfate, halides such as the chloride, bromide, and iodide, and salts of fatty acids such as acetic, propionic, butyric, valeric, capronic, oenanthic, caprylic, pelargonic, capric, undecanoic, lauric, tridecanoic, myristric, pentadecanoic, palmitic, margaric, stearic, nonadecanoic and arachidic acids, preferably the salts of the lower fatty acids. These copper salts may be added to the reaction liquid as the copper salt itself or may be formed in situ, for example, by reaction of the respective inorganic or organic acid on a part of the copper catalysts.

If the amount of these copper salts dissolved and existing in the reaction liquid is at least 5 ppm and preferably about 10 ppm, the increased yield and reaction rate of the present invention is obtained.

The effect of the copper salt is not dependent upon large concentrations of the copper salt in the reaction liquid. To the contrary, when a large amount of the copper salt is used, it provides a reverse effect by shortening the life of the copper catalyst used. For example, when about 2 percent copper nitrate is used, the activity of the copper catalyst will decrease rapidly due to a reaction between nitric acid ion and the copper salt.

Accordingly, it is preferred to adjust the amount of the copper salt existing to maintain a preferred range of 5-150 ppm of the reaction liquid calculated as cooper. If the amount exceeds 150 ppm, the production efficiency of the process decreases.

The valence state of the copper salt may be either $Cu^+$ or $Cu^{++}$. The reason therefor is that coexistence of $Cu^{++}$ with the copper catalyst within the reaction system produces the following equilibrium:

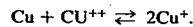

$$Cu + Cu^{++} \rightleftarrows 2Cu^+.$$

Under the ordinary reaction conditions, this equilibrium tends to be biased to the $Cu^+$ side.

The copper containing catalyst used may be Raney copper, Ullmann copper, reduced copper oxide, these catalysts supported on carriers, a copper catalyst containing metallic nickel, chromium, manganese, zine and/or molybdenum or an oxide or sulfide of copper, nickel, chromium, manganese, zinc or molybdenum.

The copper catalyst is normally used within a range of 0.01 – 1000 grams per mol of acrylonitrile or methacrylonitrile as taught in the aforementioned co-pending application.

Combinations in the catalyst system constituted by different copper salt promoters and copper containing catalysts are not limited to any particular combination and substantially the same effects are obtained with all combinations.

The amount of water vis-a-vis acrylonitrile or methacrylonitrile used in the present invention is not particularly limited and may vary depending upon the desired concentration of acrylamide or methacrylamide.

The reaction in accordance with the present invention can be carried out at room temperature (25°C.) or less. It is possible to increase the reaction rate by elevating the reaction temperature. The usual temperature range is 50° – 300°C. and preferably 50° – 150°C.

It is also possible to add a solvent to the reaction system when carrying out the present invention. Examples of suitable solvents are methanol, ethanol, isopropanol, acetone, dimethyl formamide, dimethyl sulfoxide, formamide and acetamide. By adding the aforesaid solvents to the reaction system, it is possible, for example, to increase the concentration of acrylonitrile in water.

One advantage of adding acrylamide to the reaction system in advance is the use of acrylamide as a solvent which makes possible an increase in the concentration of acrylonitrile.

Upon carrying out the present invention, it is preferable that the pH of the reaction system be neutral, mildly acid or mildly alkaline. The reason is that when using acrylonitrile as a starting material, the production of ethylene cyanhydrine, acrylic acid and/or acrylamide polymer is inhibited. However, when the reaction is carried out in accordance with the process of the present invention, in almost all cases, pH will be within the range of 5 – 9 without adding a pH control agent or a buffer solution, and it is possible to carry out the reaction without pH adjustment.

The acrylamide or methacrylamide solution obtained by the process of the present invention may be used immediately without purification because the amount of copper salt is very small. This is particularly advantageous because crystals of acrylamide or methacrylamide can be produced by merely evaporating the water. Furthermore, it is possible to immediately use these solutions to obtain polymers suitable for paper processing and other similar uses.

Of course, if necessary, it is possible to remove the copper ions by known procedures, for example, by using an ion exchange resin.

Another advantage of the present invention is to remarkably improve the reaction rate of producing acrylamide or methacrylamide from acrylonitrile or methacrylonitrile, thereby providing a process which can be carried out industrially and efficiently.

As compared with a process using a metallic copper containing catalyst alone, the process of the present invention increases the reaction rate, thereby obtaining higher conversion under the same reaction conditions and, as a result, it becomes possible to decrease the amount of expensive cooper catalyst and reduce the length of a continuous reactor.

One embodiment of an apparatus useful in preparing acrylamide or methacrylamide in accordance with the process of the present invention is explained by reference to FIG. 1.

In FIG. 1, 1 and 2 both designate Raschig ring packed towers each having a steam heater and an inlet at the bottom of the tower through which nitrogen gas is introduced. Reactor 3 has a steam heating jacket so that it can be maintained at an elevated reaction temperature and catalyst separating vessel 4 is used to separate catalyst from the reaction liquid. Water is supplied via pipe 6 to the top of packed tower 1. Through an inlet for nitrogen 15, nitrogen is blown into the packed towers 1 and 2. Through the bottom of the packed tower 1, steam is passed to heater 7, water 5 is boiled mildly and steam rises through the packed tower and is in turn condensed in condenser 14 at the top of the tower and is refluxed inside the tower. Oxygen dissolved and existing in the water is almost completely removed through evaporation and action of countercurrent contact with nitrogen. Dexoygenated water is fed through pipe 8 and cooler 12 to reactor 3 via pump 11. Acrylonitrile 9 supplied to packed tower 2 via pipe 13 is discharged after the dissolved oxygen therein is removed by the same treatment as that applied to the water, and transferred via pipe 16 to reactor 3. Raney copper catalyst which has been prepared and washed with water according to an ordinary manner is placed inside the reactor. The catalyst is vigorously stirred by stirrer 18 and mixed with the liquid reactants 19 to form a suspension phase. Liquid reaction product is separated from the catalyst in the catalyst separating vessel 4 and withdrawn from the system via pipe 10. The catalyst which has precipitated at the bottom of catalyst separating vessel 4 is returned to reactor 3 by pump 17. It is preferable to replace the air inside reactor 3 and catalyst separating vessel 4 with nitrogen prior to the reaction and separation steps.

The following embodiments are illustrative of the present invention.

EXAMPLE 1

An experiment was conducted using the apparatus shown in FIG. 1.

Copper nitrate was added to water in an amount of 10 ppm calculated as $Cu^{++}$. From pipe 6, the water was supplied at a rate of 700 g/hr and from pipe 13, acrylonitrile was supplied at a rate of 140 g/hr. The reaction temperature was 120°C. and the average residence time inside the reactor was 60 minutes. The amount of Raney copper catalyst inside the reactor was 240 grams and the reactor was maintained under a pressure of 4 kg/cm$^2$ gauge by nitrogen.

Gas chromatography analysis of the reaction liquid produced showed 40 g/hr of acrylonitrile and 134 g/hr of acrylamide with no other product than acrylamide, and no side reactions.

This value represented a conversion of 71.5% with respect to acrylonitrile. For about 3 days the reaction was maintained under these conditions. One analysis of copper in the reaction liquid showed the amount of $Cu^+$ was 13.5 ppm and the amount of $Cu^{++}$ was very small. The pH of the reaction liquid was 6.5.

The quantitative determination of copper ion was carried out by polarography. Namely, $Cu^+$ showed a one-stage reduction wave corresponding to the reaction of $Cu^+ \rightarrow Cu°$, and $Cu^{++}$ showed a two-stage reduction wave corresponding to $Cu^{++} \rightarrow Cu^+ \rightarrow Cu°$. Therefore, $Cu^{++}$ was determined by a first stage wave and $Cu^+$ plus $Cu^{++}$ were determined by a second stage wave.

For purposes of comparision, the amount of copper nitrate in the water was increased so that the amount of $Cu^{++}$ became 100 ppm and the reaction was continued. The result of analyzing the reaction liquid after 8 hours shows that conversion of acrylonitrile to acrylamide was 68.4%. Analysis of copper in the reaction liquid at that time showed that the amount of $Cu^+$ was 160 ppm and the amount of $Cu^{++}$ was very small.

When the aforesaid experiment was repeated without adding copper nitrate to the water, conversion of acrylonitrile to acrylamide remained at about 48 – 50% for about 3 days after the reaction was initiated.

EXAMPLE 2

Into a four-necked 100 ml flask were introduced 2 grams of Raney copper which had been prepared and washed with water, 25.0 grams of acrylonitrile and 25.0 grams of water into which copper sulfate was dissolved so that the amount of $Cu^{++}$ ion provided was 50 ppm, and the mixture was refluxed at a reaction temperature of about 70°C. for 2 hours, while being stirred in a nitrogen atmosphere.

Results of analyzing the reaction liquid produced by gas chromatography showed that conversion of acrylonitrile to acrylamide was 34.3% and other by-products were not produced.

When Example 1 was repeated using copper sulfate instead of copper nitrate, conversion of acrylonitrile to acrylamide was maintained at 67 – 70% for the first 3 days and products other than acrylamide could not be identified by gas chromatography.

When the aforesaid experiment was repeated without adding copper sulfate for the purpose of comparison, it was found that conversion of acrylonitrile to acrylamide was only 24.2%.

EXAMPLE 3

Instead of copper sulfate in Example 2, cupric chloride was used in conducting a similar experiment and the mixture was refluxed for 2 hours.

Results of analyzing by gas chromatography the reaction liquid produced showed that conversion of acrylonitrile to acrylamide was 32.2% and other by-products were not recognized.

Conversion of acrylonitrile to acrylamide 1 hour after the start of the reaction was 18.1%.

When the aforesaid experiment was repeated without adding cupric chloride for the purpose of comparison, conversion of acrylonitrile to acrylamide 1 hour after the start of the reaction was 13.0%.

EXAMPLE 4

In a four-necked 100 ml flask were introduced 2 grams of Raney copper which had been prepared and washed with water, 26.5 grams of acrylonitrile and 18.0 grams of water in which copper acetate was dissolved so that the amount of $Cu^{++}$ ion was 100 ppm and the mixture was refluxed for 2 hours at a reaction temperature of 70°C. while being stirred in a nitrogen atmosphere.

Results of analyzing by gas chromatography the reaction liquid produced showed that conversion of acrylonitrile to acrylamide was 18.3% and other by-products were not shown to be present.

When the aforesaid experiment was repeated without adding copper acetate for the purpose of comparison, it was found that conversion of acrylonitrile to acrylamide was 13.2%.

EXAMPLE 5

Ten grams of cupric oxide produced from copper nitrate and caustic soda was reduced with 100 cc/min of hydrogen at 200 – 250°C. for 4 hours. 6.6 Grams of acrylonitrile and 36.2 grams of water were added to the resultant catalyst and the water included copper acetate corresponding to a copper ion content of 50 ppm. The mixture was reacted at 70°C. in a nitrogen atmosphere for 2 hours.

Results of analyzing the reaction liquid produced by gas chromatography showed that conversion of acrylonitrile to acrylamide was 57.2% and other by-products were barely perceptable.

When the aforesaid experiment was repeated without adding copper acetate for the purpose of comparision, it was found that conversion of acrylonitrile to acrylamide was 45.3%.

EXAMPLE 6

In the presence of a catalyst of 10 grams of Ullmann copper prepared by the established process, 6.6 grams of acrylonitrile and 36.0 grams of water containing copper nitrate so that the amount of copper ion was 50 ppm were added to a reactor and the mixture was reacted at 70°C. in a nitrogen atmosphere for 2 hours.

Results of analyzing the reaction liquid produced by gas chromatography showed that conversion of acrylonitrile to acrylamide was 38.9% and other by-products were not shown.

When the aforesaid reaction was repeated without adding copper nitrate for purposes of comparision, it was found that conversion of acrylonitrile to acrylamide was 25.5%.

EXAMPLES 7 – 10

2 Grams of Raney copper which had been prepared and washed with water and 4.2 grams of methacrylonitrile and 36.0 grams of water were charged into a four-necked 100 ml flask, and the mixture was reacted at a temperature of about 80°C. under atmospheric pressure with stirring.

The results obtained by adding the following copper salts to said water so that the amounts of copper might become 50 ppm are shown in the following table together with a comparative example showing no addition.

Table 1

| Example | Copper Salt | Amount of Methacrylamide Produced (g) |
|---|---|---|
| 7 | Copper sulfate | 4.6 |
| 8 | Copper nitrate | 4.8 |
| 9 | Copper acetate | 4.5 |
| 10 | Cupric chloride | 4.6 |
| Comp. | None | 4.1 |

EXAMPLE 11

Using an apparatus the same as in Example 1 and charging 22 grams of Raney copper as catalyst, a reaction was carried out under the same conditions as those of Example 1. 14 Hours after the start of the reaction, the concentration of copper nitrate calculated as $Cu^{++}$ was increased from 10 ppm to 500 ppm and the reaction was carried out for an additional 16 hours.

During the two periods, conversions of acrylonitrile to acrylamide changed as shown in the following table, showing that an excess amount of copper nitrate shortens the life of the catalyst.

Table 2

| Operating Time (hr) | Amount of Cu++ in Water (ppm) | Acrylonitrile Conversion (%) |
|---|---|---|
| 4 | 10 | 35.0 |
| 8 | " | 33.6 |
| 12 | " | 29.0 |
| 14 | " | 28.3 |
| 18 | 500 | 19.7 |
| 22 | " | 10.2 |
| 26 | " | 2.5 |
| 30 | " | 1.4 |

EXAMPLES 12 – 15

22 Grams of a Raney cooper catalyst was introduced into a reactor of the same type as used in Example 1, to which were fed water which contained copper nitrate in a quantity corresponding to 5 ppm of copper ion and acrylonitrile in feeding rates of 700 g/hr and 1400 g/hr, respectively, for reaction at 120°C. The reaction was continued for 16 hours, during which the reaction solution was analyzed at predetermined intervals of time periods to determine the conversion of acrylonitrile into acrylamide.

Further, the above process was repeated using copper sulfate, copper acetate and cupric chloride and was further repeated as a comparative example with no salt added. The test results are shown in the following table, from which it will be understood that the use of any copper salt provides a remarkable effect on the conversion.

Table 3

| Example | Copper Salt | Conversion of Acrylonitrile into Acrylamide (%) Reaction Time (hrs) | | | |
|---|---|---|---|---|---|
| | | 4 | 8 | 12 | 16 |
| 12 | Copper nitrate | 30 | 28 | 26 | 26 |
| 13 | Copper sulfate | 28 | 27 | 25 | 23 |
| 14 | Copper acetate | 28 | 26 | 25 | 22 |
| 15 | Cupric chloride | 29 | 28 | 25 | 23 |
| Comp. | None | 19 | 17 | 16 | 16 |

EXAMPLE 16

A solution of 3.8 grams of $Cu(NO_3)_2 \cdot 3H_2O$ in 100 ml of water was added at room temperature to a solution of 4.0 grams of $NaBH_4$ in 200 ml of water thereby forming a cotton-like black precipitate. The thus formed precipitate was separated from the solution by decantation and then washed several times with water in amounts substantially equal to the separated solution to obtain about 1 gram of a reduced copper catalyst.

Thereafter, the procedure of Examples 12 – 15 was repeated using the thus obtained reduced copper catalyst. The test results are shown in the following table.

Table 4

| Copper Salt | Conversion of Acrylonitrile into Acrylamide (%) Reaction Time (hrs) | | | |
|---|---|---|---|---|
| | 4 | 8 | 12 | 16 |
| Copper nitrate | 36 | 32 | 30 | 29 |
| None | 23 | 20 | 20 | 18 |

EXAMPLES 17 AND 18

300 Grams of copper-chromium catalyst (tablet of $CuO + CuCr_2O_4$, N-201 made by Nikki Chemical Company) was packed in a tubular reactor (stainless steel SUS-304) having an internal diameter of 30 mm and was reduced with a mixture of nitrogen gas containing 2% of hydrogen which was preheated to 180°C. and fed at the rate of 60 l/min. for 14 hours. Acrylonitrile and water were treated in deoxygenating apparatus to remove about 90% of dissolved oxygen, and were fed to the reactor at the rates of 270 and 670 gr/hr., respectively. The reacting solution was circulated at the rate of 40 l/hr. in a manner so that the solution flowing out of the top of the reactor was recirculated to the bottom thereof by a pump. The reaction was carried out for 10 days keeping the reactor at about 120°C. Another run was repeated in the same way except that the water contained 14 ppm of cupric ion using cupric nitrate. The conversion of acrylonitrile to acrylamide in the above two runs is shown in the following table.

Table 5

| Operating Time | Conversion (%) | |
|---|---|---|
| | No Addition of Copper nitrate | Addition |
| 1 day | 52 | 71 |
| 2 days | 45 | 61 |
| 4 days | 40 | 53 |
| 6 days | 33 | 48 |
| 10 days | 30 | 43 |

Next, 300 grams of copper-zinc catalyst (tablet of CuO + ZnO, N-211 made by Nikki Chemical Company) was packed in the same reactor and was reduced in the same way as above. Two runs were carried out in the same way as above using pure water and 14 ppm cupric ion solution (cupric nitrate was added as cupric ion) and the results obtained are shown in the following table.

Table 6

| Operating Time | Conversion (%) | |
|---|---|---|
| | No Addition of Copper nitrate | Addition |
| 1 day | 46 | 63 |
| 2 days | 38 | 55 |
| 4 days | 34 | 45 |
| 6 days | 29 | 41 |
| 10 days | 27 | 38 |

In the above two examples, cupric nitrate was found to be an effective promoter.

EXAMPLE 19

300 Grams of copper oxide (tablet of CuO, made by Nikki Chemical Company) was packed in a tubular reactor (stainless steel SUS-304) having an internal diameter of 30 mm and was reduced with a mixture of nitrogen gas containing 2% of hydrogen preheated to 180°C. and fed at the rate of 60 l/min. for 14 hours. Acrylonitrile and water were treated in deoxygenating apparatus to remove about 90% of dissolved oxygen, and were fed to the reactor at the rates of 270 and 670 gr/hr, respectively. The reacting solution was circulated at the rate of 40 l/hr. in such a manner that the solution flowing out of the top of the reactor was recirculated to the bottom by a pump. The reaction was carried out for 16 hours keeping the reactor at about 120°C. Another run was repeated in the same way except that the water contained 7 ppm of cupric ion using cupric nitrate. The conversion of acrylonitrile to acrylamide in the above two runs is shown in the following table.

Table 7

| Operating Time | Conversion (%) | |
|---|---|---|
| | No Addition of Copper nitrate | Addition |
| 4 hours | 55 | 69 |
| 8 hours | 53 | 67 |
| 12 hours | 51 | 66 |
| 16 hours | 50 | 64 |

What is claimed is:

1. In a process for preparing acrylamide or methacrylamide by reacting acrylonitrile or methacrylonitrile with water in the presence of a metallic copper containing catalyst, the improvement comprising adding to the reaction liquid a promoter for said catalyst, said promoter being selected from the group consisting of copper sulfate, copper nitrate, cupric chloride and a copper salt of a lower fatty acid, in an amount of from 5 to 150 ppm calculated as copper and based upon available water.

2. The improvement of claim 1 wherein said metallic copper containing catalyst is selected from the group consisting of Raney copper, Ullmann copper, reduced copper, reduced copper oxide and copper containing (a) at least one metal selected from the group consisting of chromium and zinc or (b) a reduced oxide of said metal.

3. The improvement of claim 1 wherein said copper salt is selected from the group consisting of copper acetate, copper propionate, copper butyrate, copper valerate, copper caproate and copper oenanthate.

4. The improvement of claim 2 wherein said copper salt is selected from the group consisting of copper acetate, copper propionate, copper butyrate, copper valerate, copper caproate and copper oenanthate.

5. A continuous process for preparing acrylamide or methacrylamide which comprises reacting acrylonitrile or methacrylonitrile with water at a temperature of about 50° – 300°C. in the presence of 0.01 to 1000 g. per mol of acrylonitrile or methacrylonitrile of a copper catalyst selected from the group consisting of Raney copper, Ullmann copper, reduced copper, reduced copper oxide, and copper containing (a) at least one metal selected from the group consisting of chromium and zinc or (b) a reduced oxide of said metal, and adding to the reaction liquid a promoter selected from the group consisting of copper sulfate, copper nitrate and cupric chloride in an amount of about 5 to 150 ppm calculated as copper and based upon available water.

* * * * *